United States Patent
Schofield et al.

(10) Patent No.: US 6,924,362 B2
(45) Date of Patent: Aug. 2, 2005

(54) MONOCLONAL ANTIBODIES SPECIFIC FOR THE E2 GLYCOPROTEIN OF HEPATITIC C VIRUS AND THEIR USE IN THE DIAGNOSIS, TREATMENT, AND PREVENTION OF HEPATITIS C

(75) Inventors: Darren Schofield, Royston (GB); Suzanne U. Emerson, Kensington, MD (US); Robert H. Purcell, Boyds, MD (US); Harvey J. Alter, Chevy Chase, MD (US)

(73) Assignee: The United States of America as represented by the Department of Health & Human Services, Washington, DC (US)

( * ) Notice: Subject to any disclaimer, the term of this patent is extended or adjusted under 35 U.S.C. 154(b) by 0 days.

(21) Appl. No.: 10/432,006
(22) PCT Filed: Nov. 30, 2001
(86) PCT No.: PCT/US01/45221
§ 371 (c)(1), (2), (4) Date: Dec. 15, 2003
(87) PCT Pub. No.: WO02/055560
PCT Pub. Date: Jul. 18, 2002

(65) Prior Publication Data
US 2004/0115619 A1 Jun. 17, 2004

Related U.S. Application Data
(60) Provisional application No. 60/250,561, filed on Dec. 1, 2000.

(51) Int. Cl.[7] .................... C07K 16/00; A61K 39/395; A61K 39/42; C12Q 1/70; G01N 33/53
(52) U.S. Cl. .................. 530/388.3; 530/387.1; 530/388.1; 424/141.1; 424/147.1; 424/149.1; 435/5; 435/7.1; 435/69.1
(58) Field of Search ................ 530/388.3, 388.1; 424/133.1, 130.1, 139.1, 141.1, 147.1, 149.1; 435/5, 7, 69.1

(56) References Cited

U.S. PATENT DOCUMENTS

| | | | | |
|---|---|---|---|---|
| 5,308,750 A | * | 5/1994 | Mehta et al. | 435/5 |
| 6,521,403 B1 | * | 2/2003 | Maertens et al. | 435/5 |
| 6,538,114 B1 | * | 3/2003 | Persson et al. | 530/388.3 |
| 6,692,908 B1 | * | 2/2004 | Foung et al. | 435/5 |

FOREIGN PATENT DOCUMENTS

| WO | WO 97/40176 | 10/1997 |
|---|---|---|
| WO | WO 98/16647 | 4/1998 |

OTHER PUBLICATIONS

Allander T. et al. 2000 Recombinant human monoclonal antibodies against different conformational epitopes of the E2 envelope glycoprotein of hepatitis C virus that inhibit its interaction with CD81. *J Gen Virol.* 81(Pt10):2451–2459.

Burioni R. et al. 1998 Dissection of human humoral immune response against hepatitis C virus E2 glycoprotein by repertoire cloning and generation of recombinant Fab fragments. *Hepatology* 28(3):810–814.

Chan SW. et al. 1996 Human recombinant antibodies specific for hepatitis C virus core and envelope E2 peptides from an immune phage display library. *J Gen Virol.* 77(Pt10):2531–2539.

Farci P. et al. 1994 Prevention of hepatitis C virus infection in chimpanzees after antibody–mediated in vitro neutralization. *PNAS USA* 91(16):7792–7796.

Farci P. et al. 1996 Prevention of hepatitis C virus infection in chimpanzees by hyperimmune serum against the hypervariable region 1 of the envelope 2 protein. *PNAS USA* 93(26):15394–15399.

Hadlock KG. et al. 2000 Human monoclonal antibodies that inhibit binding of hepatitis C virus E2 protein to CD81 and recognize conserved conformational epitopes. *J Virol.* 74(22):10407–10416.

Plaisant P. et al. 1997 Human monoclonal recombinant Fabs specific for HCV antigens obtained by repertoire cloning in phage display combinatorial vectors. *Res Virol.* 148(2):165–169.

Shimizu YK. et al. 1996 A hyperimmune serum against a synthetic peptide corresponding to the hypervariable region 1 of hepatitis C virus can prevent viral infection in cell cultures. *Virology.* 223(2):409–412.

Zhai W. et al. 1999 Human recombinant single–chain antibody fragments, specific for the hypervariable region 1 of hepatitis C virus, from immune phage–display libraries. *J Viral Hepat.* 6(2):115–24.

* cited by examiner

Primary Examiner—James Housel
Assistant Examiner—Michael M. McGaw
(74) Attorney, Agent, or Firm—Knobbe, Martens, Olson & Bear LLP

(57) ABSTRACT

The present invention describes the identification and characterization of five human HC E1-specific monoclonal antibodies isolated from a phage display library and their use in the diagnosis, treatment, and prevention of HCV in mammals, preferably humans.

16 Claims, 3 Drawing Sheets

FIGURE 1

| MAb | FR1 | CDR1 | FR2 |
|---|---|---|---|
| HCV#1 | EVQLLE-SGPGLVKPSQTLSLTCTVSGASIS | SDSYYYN | WIRQPAGKGLEWIG |
| HCV#4 | EVQLLEQSGAEVKKPGSAVKVSCKASGGNFN | IDTIS | WLRQVPGQGLEWMG |
| HCV#7 | EVQLLEQSGAEVKKPGSSVKVSCTASGGTFT | THTIN | WVRQAPGNGLEWMG |
| HCV#12 | EVQLLEQSGAEVKKPGSSVKVFCKASGGIFY | ISTIN | WVRQAPGQGLEWMG |
| HCV#13 | EVQLLE-SGPGLVKPSETLSLTCTVSGGSLS | GYYWT | WIRQPPGKGLEWIG |

| MAb | CDR2 | FR3 |
|---|---|---|
| HCV#1 | RIYTSGSTNYNPSLKG | RLTISVDTSKNQFSLKLTSVTAADTAVYYCAR |
| HCV#4 | RIIPIVTMTNYAETFQG | RVTITADRSTSTVYMELRSLRSEDTAVYYCAR |
| HCV#7 | QIIPLVGMTNIAQQFEG | RITIIADKATSTAYMELSSLGSEDTALYYCAR |
| HCV#12 | KIIPGVGMTNFAQKFQG | RVTITADKSTNTVYLEVSSLRSEDTAVYYCAT |
| HCV#13 | YMYWSGSTNYSPSLKS | RLTLSADTSKNHLSLKLTSVTAADTAVYYCGR |

| MAb | CDR3 | FR4 |
|---|---|---|
| HCV#1 | TGRFLEWFPNYGMDV | WGQGSTVIVSS |
| HCV#4 | SISDTGLFRLDAFDS | WGPGTRVIVSS |
| HCV#7 | SLATSGLFRVDAFDL | WGQGTMVTVSS |
| HCV#12 | SRPDTGLFRKDAFDV | WGQGTVVIVSS |
| HCV#13 | LSRTVTMIDN | WGQGILVTVSP |

FIGURE 3
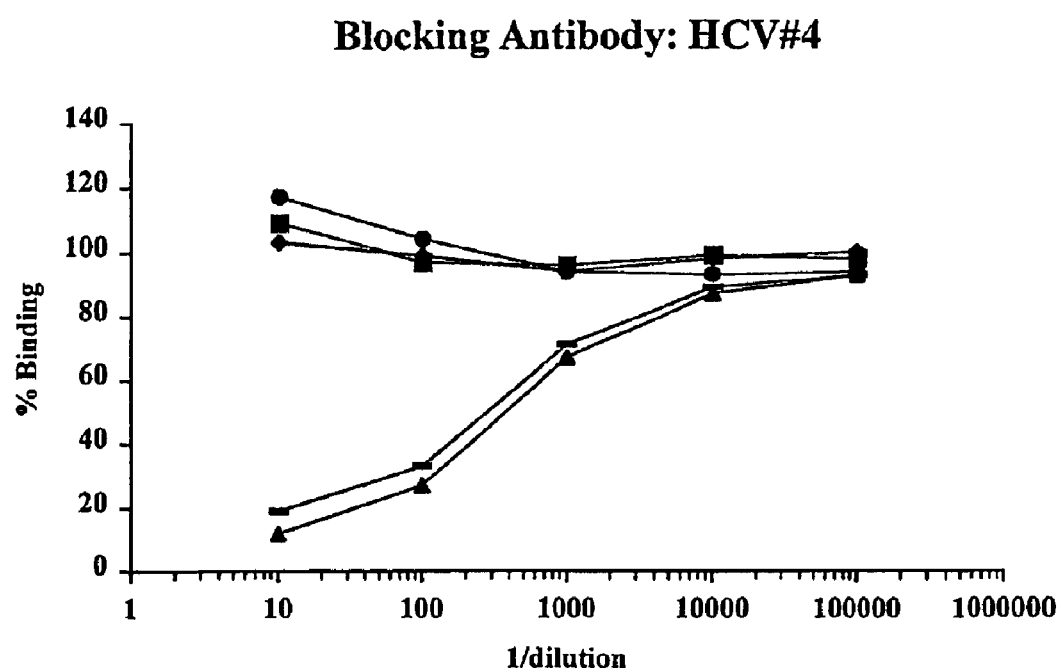
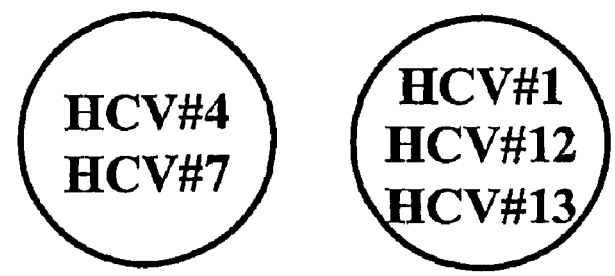

SEQUENCE LISTING

```
<160> NUMBER OF SEQ ID NOS: 9

<210> SEQ ID NO 1
<211> LENGTH: 125
<212> TYPE: PRT
<213> ORGANISM: Homo sapiens

<400> SEQUENCE: 1

Glu Val Gln Leu Leu Glu Ser Gly Pro Gly Leu Val Lys Pro Ser Gln
 1               5                   10                  15

Thr Leu Ser Leu Thr Cys Thr Val Ser Gly Ala Ser Ile Ser Ser Asp
            20                  25                  30

Ser Tyr Tyr Tyr Asn Trp Ile Arg Gln Pro Ala Gly Lys Gly Leu Glu
        35                  40                  45

Trp Ile Gly Arg Ile Tyr Thr Ser Gly Ser Thr Asn Tyr Asn Pro Ser
    50                  55                  60
```

-continued

Leu Lys Gly Arg Leu Thr Ile Ser Val Asp Thr Ser Lys Asn Gln Phe
65                  70                  75                  80

Ser Leu Lys Leu Thr Ser Val Thr Ala Ala Asp Thr Ala Val Tyr Tyr
                85                  90                  95

Cys Ala Arg Thr Gly Arg Phe Leu Glu Trp Phe Pro Asn Tyr Gly Met
            100                 105                 110

Asp Val Trp Gly Gln Gly Ser Thr Val Ile Val Ser Ser
        115                 120                 125

<210> SEQ ID NO 2
<211> LENGTH: 125
<212> TYPE: PRT
<213> ORGANISM: Homo sapiens

<400> SEQUENCE: 2

Glu Val Gln Leu Leu Glu Gln Ser Gly Ala Glu Val Lys Lys Pro Gly
1               5                   10                  15

Ser Ala Val Lys Val Ser Cys Lys Ala Ser Gly Gly Asn Phe Asn Ile
            20                  25                  30

Asp Thr Ile Ser Trp Leu Arg Gln Val Pro Gly Gln Gly Leu Glu Trp
        35                  40                  45

Met Gly Arg Ile Ile Pro Ile Val Thr Met Thr Asn Tyr Ala Glu Thr
    50                  55                  60

Phe Gln Gly Arg Val Thr Ile Thr Ala Asp Arg Ser Thr Ser Thr Val
65                  70                  75                  80

Tyr Met Glu Leu Arg Ser Leu Arg Ser Glu Asp Thr Ala Val Tyr Tyr
                85                  90                  95

Cys Ala Arg Ser Ile Ser Asp Thr Gly Leu Phe Arg Leu Asp Ala Phe
            100                 105                 110

Asp Ser Trp Gly Pro Gly Thr Arg Val Ile Val Ser Ser
        115                 120                 125

<210> SEQ ID NO 3
<211> LENGTH: 125
<212> TYPE: PRT
<213> ORGANISM: Homo sapiens

<400> SEQUENCE: 3

Glu Val Gln Leu Leu Glu Gln Ser Gly Ala Glu Val Lys Lys Pro Gly
1               5                   10                  15

Ser Ser Val Lys Val Ser Cys Thr Ala Ser Gly Gly Thr Phe Thr Thr
            20                  25                  30

His Thr Ile Asn Trp Val Arg Gln Ala Pro Gly Asn Gly Leu Glu Trp
        35                  40                  45

Met Gly Gln Ile Ile Pro Leu Val Gly Met Thr Asn Ile Ala Gln Gln
    50                  55                  60

Phe Glu Gly Arg Ile Thr Ile Ile Ala Asp Lys Ala Thr Ser Thr Ala
65                  70                  75                  80

Tyr Met Glu Leu Ser Ser Leu Gly Ser Glu Asp Thr Ala Leu Tyr Tyr
                85                  90                  95

Cys Ala Arg Ser Leu Ala Thr Ser Gly Leu Phe Arg Val Asp Ala Phe
            100                 105                 110

Asp Leu Trp Gly Gln Gly Thr Met Val Thr Val Ser Ser
        115                 120                 125

<210> SEQ ID NO 4
<211> LENGTH: 125

```
<212> TYPE: PRT
<213> ORGANISM: Homo sapiens

<400> SEQUENCE: 4

Glu Val Gln Leu Leu Glu Gln Ser Gly Ala Glu Val Lys Lys Pro Gly
 1               5                  10                  15

Ser Ser Val Lys Val Phe Cys Lys Ala Ser Gly Gly Ile Phe Tyr Ile
            20                  25                  30

Ser Thr Ile Asn Trp Val Arg Gln Ala Pro Gly Gln Gly Leu Glu Trp
        35                  40                  45

Met Gly Lys Ile Ile Pro Gly Val Gly Met Thr Asn Phe Ala Gln Lys
50                  55                  60

Phe Gln Gly Arg Val Thr Ile Thr Ala Asp Lys Ser Thr Asn Thr Val
65                  70                  75                  80

Tyr Leu Glu Val Ser Ser Leu Arg Ser Glu Asp Thr Ala Val Tyr Tyr
                85                  90                  95

Cys Ala Thr Ser Arg Pro Asp Thr Gly Leu Phe Arg Lys Asp Ala Phe
            100                 105                 110

Asp Val Trp Gly Gln Gly Thr Val Val Ile Val Ser Ser
        115                 120                 125

<210> SEQ ID NO 5
<211> LENGTH: 117
<212> TYPE: PRT
<213> ORGANISM: Homo sapiens

<400> SEQUENCE: 5

Glu Val Gln Leu Leu Glu Ser Gly Pro Gly Leu Val Lys Pro Ser Glu
 1               5                  10                  15

Thr Leu Ser Leu Thr Cys Thr Val Ser Gly Gly Ser Leu Ser Gly Tyr
            20                  25                  30

Tyr Trp Thr Trp Ile Arg Gln Pro Pro Gly Lys Gly Leu Glu Trp Ile
        35                  40                  45

Gly Tyr Met Tyr Trp Ser Gly Ser Thr Asn Tyr Ser Pro Ser Leu Lys
50                  55                  60

Ser Arg Leu Thr Leu Ser Ala Asp Thr Ser Lys Asn His Leu Ser Leu
65                  70                  75                  80

Lys Leu Thr Ser Val Thr Ala Ala Asp Thr Ala Val Tyr Tyr Cys Gly
                85                  90                  95

Arg Leu Ser Arg Thr Val Thr Met Ile Asp Asn Trp Gly Gln Gly Ile
            100                 105                 110

Leu Val Thr Ser Pro
        115

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
attgcctacg gcagccgctg g                                           21

<210> SEQ ID NO 7
<211> LENGTH: 21
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 7
ggaagtagtc cttgaccagg c                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
acagctatcg cgattgcagt g                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cacctgatcc tcagatggcg g                                              21
```

MONOCLONAL ANTIBODIES SPECIFIC FOR THE E2 GLYCOPROTEIN OF HEPATITIC C VIRUS AND THEIR USE IN THE DIAGNOSIS, TREATMENT, AND PREVENTION OF HEPATITIS C

RELATED APPLICATIONS

This application represents the U.S. National Phase of International Application No. PCT/US01/45221 filed Nov. 30, 2001, designating the United States of America and published in English, which claims the benefit of priority of U.S. Provisional Application No. 60/250,561 filed Dec. 1, 2000, which is hereby expressly incorporated by reference in its entirety.

FIELD OF THE INVENTION

The present invention is in the field of hepatitis virology. More specifically, the invention relates to monoclonal antibodies specific for the envelope 2 (E2) protein of hepatitis C virus (HCV) and the use of these antibodies in the diagnosis, treatment, and prevention of hepatitis C.

BACKGROUND OF THE INVENTION

Hepatitis C, originally called non-A, non-B hepatitis, was first described in 1975 as a disease serologically distinct from hepatitis A and hepatitis B (Feinstone, S. M. et al. (1975) *N. Engl. J. Med.*, 292:767–770). Although hepatitis C remains the leading type of transfusion-associated hepatitis as well as an important part of community-acquired hepatitis, little progress was made in understanding the disease until the identification of hepatitis C virus (HCV) as the causative agent of hepatitis C via the cloning and sequencing of the HCV genome (Choo, A. L. et al. (1989) *Science*, 288:359–362). From the sequence information generated by this study, HCV was characterized as a small, enveloped, positive-stranded RNA virus.

HCV is a major cause of both acute and chronic hepatitis worldwide (Weiner, A. J. et al. (1990) *Lancet*, 335:1–3). Approximately 80% of individuals acutely infected with HCV become chronically infected and more than 20% of these individuals eventually develop liver cirrhosis (Alter, H. J. Seeff, L. B.: *Transfusion Associated Hepatitis*, In: Zuckerman, A. J. Thomas, H. C. (eds): *Viral Hepatitis: Scientific Basis and Clinical Management*, Edinburgh Churchill Livingstone, 1993). In a vast majority of infected individuals, HCV causes a chronic disease leading to loss of liver function, and, without a liver transplant, ultimately to death. Post-transplant patients are still at risk from re-infection of the new liver from circulating HCV. In addition, a strong association has been found between HCV infection and the development of hepatocellular carcinoma (Bukh et al. (1993) *Proc. Natl. Acad. Sci. USA*, 90:1848–1851). HCV infection also seems to be associated with other diseases, including some autoimmune diseases (Manns, M. P. (1993) *Intervirol.*, 35:108–115; Lionel, F. (1994) *Gastroenterology.* 107:1550–1555). Thus, significant morbidity and mortality is caused by HCV infection worldwide. Presently, there is no immunoprophylaxis or immunotherapy to prevent and/or treat HCV infection and in addition, current drug therapies are only partially effective. Therefore development of an effective immunoprophylaxis or immunotherapy is of high priority.

The hepatitis C virus contains three putative structural proteins, consisting of the N-terminal nucleocapsid protein (termed "core") and two envelope glycoproteins, "E1" and "E2". (See, Houghton et al. (1991) *Hepatology*, 14:381–388).

The HCV E1 and E2 proteins are of considerable interest in immunoprophylactic and immunotherapy development. Indeed, recombinant vaccines based on these molecules have been shown to be protective against experimental challenge with HCV in primate studies. Specifically, Choo et al. ((1994) *Proc. Natl. Acad. Sci. USA*, 91:1294–98), using recombinant E1 and E2 proteins of HCV-1 as immunogens, reported the successful vaccination of chimpanzees against challenge with the homologous strain of HCV. However, Choo et al. did not demonstrate protection against challenge with a heterologous strain of HCV and the discovery of the extraordinary diversity of HCV genomes based on sequence analysis of numerous HCV isolates (Bukh et al.; *Proc. Natl. Acad. Sci. USA*, (1993) 90:8234–8238, Bukh et al. (1994) *Proc. Natl. Acad. Sci. USA*, 91:8239–8243) suggests that a successful vaccine must protect against challenge by multiple strains of HCV. This conclusion is supported by the work of both Farci et al. (Farci, P. et al. (1992) *Science*, 258:135–140) and Prince et al. (Prince, A. M. et al. (1992) *J. Infect. Dis.*, 165:438–443), each of whom presented evidence that while infection with one strain of HCV modifies the degree of the hepatitis C associated with the reinfection, it does not protect against reinfection with a closely related strain.

Since antibodies elicited to HCV may neutralize the infectivity of the virus (Shimizu et al. (1994) *J. Virol.*, 68:1494–1500; Farci et al. (1994) *Proc. Natl. Acad. Sci. USA*, 91:7792–96), the administration of a highly reactive, neutralizing anti-HCV antibody preparation to an individual who is at risk of infection, or who has recently been exposed to the infectious agent, may provide passive immunity to the immunized individual.

Thus, there is a need for antibodies directed against HCV which may be used for protecting individuals who are at high risk from HCV infection, or who have recently been exposed to HCV. Preferably, the neutralizing antibodies would be broadly cross-reactive against different HCV strains.

SUMMARY OF THE INVENTION

The present invention relates to human monoclonal antibodies which exhibit immunological binding affinity for hepatitis C virus (HCV) E2 polypeptide antigen, and are cross-reactive against different HCV strains.

The present invention also relates to the amino acid sequences of the FRs and CDRs of the γ1 chains of these antibodies and to nucleic acid molecules that encode these amino acid sequences.

The present invention further relates to the combinatorial library, from which the specific antibodies described herein are obtained, since the library may provide a repository of additional monoclonal antibodies against HCV proteins.

The invention therefore also relates to monoclonal antibodies, which may be isolated from this library, wherein such antibodies may include antibodies to HCV E2 polypeptide as well as antibodies to other HCV polypeptides.

Also, the present invention relates to the use of the monoclonal antibodies of the invention in the development of prophylactic, therapeutic, and diagnostic agents for the prevention, treatment, and detection of hepatitis in mammals, preferably humans.

Further, the present invention relates to a kit comprising the antibodies of the present invention for use as a therapeutic, prophylactic, or diagnostic agent.

These, and other objects of the invention, will be more fully understood after a consideration of the following description of the invention.

BRIEF DESCRIPTION OF THE FIGURES

FIG. 1 shows the amino acid sequence of the FRs and CDRs of the γ1-chains of five E2-specific monoclonal antibodies, designated HCV#1 (SEQ ID NO:1); HCV#4 (SEQ ID NO:2); HCV#7 (SEQ ID NO:3); HCV#12 (SEQ ID NO:4); HCV#13 (SEQ ID NO:5), wherein FR refers to framework region and CDR refers to the complementarity-determining region.

FIG. 3 shows the results of epitope mapping by indirect competition ELISA of the five monoclonal antibodies on the E2 protein. Unlabelle HCV#4 Fab was reacted with B2-coated ELISA wells, and the binding of biotinylated HCV#1 (●), HCV#4 (Δ), HCV#7 (■), HCV#12 (■), and HCV#13 (♦) was detected with a streptavidin-alkaline phosphatase conjugate. Unlabelled HCV#4 inhibited the binding of biotinylated HCV#4 and HCV#7 to E2-coated wells.

DETAILED DESCRIPTION OF THE INVENTION

Figure 2:
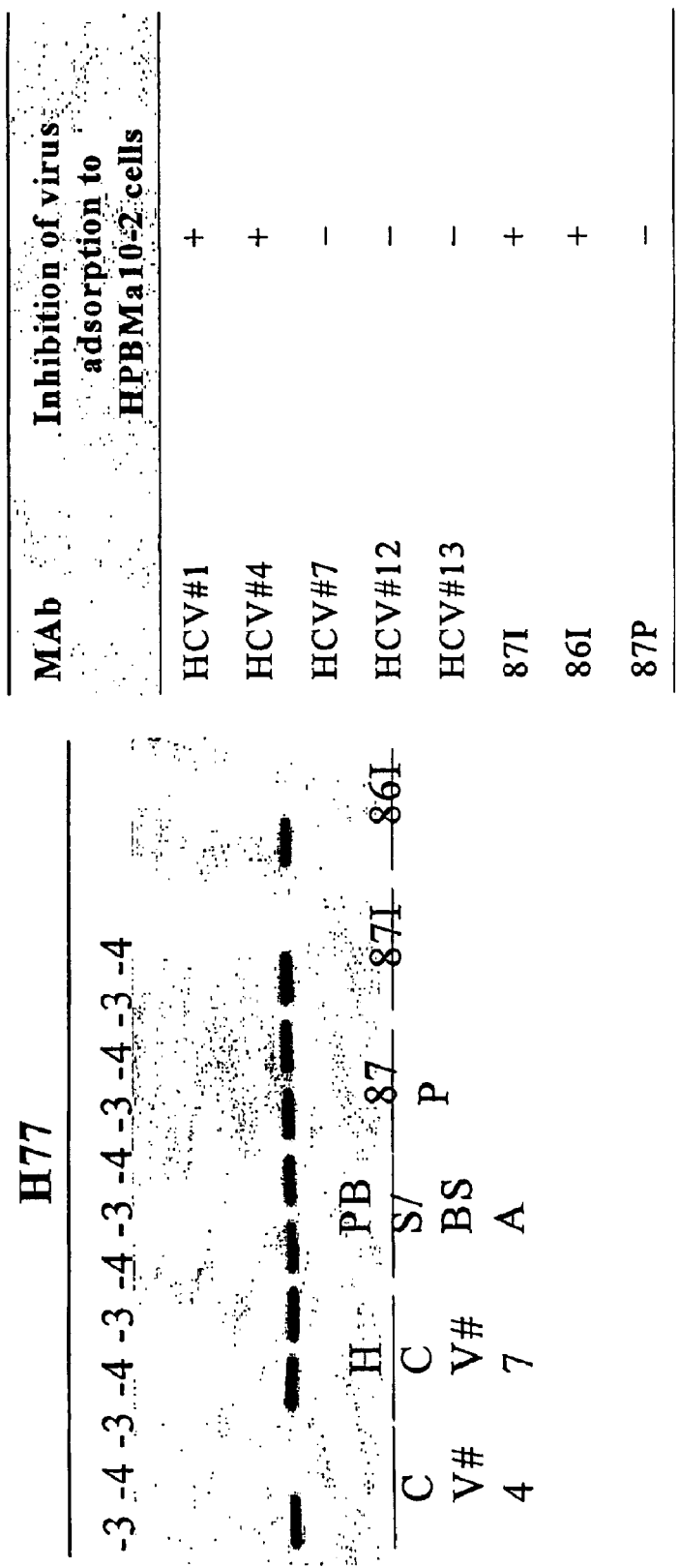
FIG. 2 shows the results of a neutralization of binding (NOB) adsorption-inhibition assay depicting inhibition of adsorption of virus innoculum from patient H(H77) to HPBMa10-2 cells, a human T-cell line susceptible to HCV infection. HCV#4 reduced the titer of cell-associated virus, however there was no reduction in PCR titer with HCV#7. Therefore, HCV#4 blocked HCV adsorption to HPBMa10-2 cells. Rabbit hyper-immune sera, 86I and 87I, were used as positive controls for the inhibition of HCV adsorption to cells. Rabbit pre-immune serum 87P was a negative control.

The present invention relates to five human monoclonal antibodies which exhibit immunological binding affinity for HCV E2, wherein the antibodies are isolated as Fab fragments from a phage display library prepared from bone marrow lymphocyte and plasma cell RNAs isolated from an asymptomatic chronically HCV infected patient (patient H). In particular, the antibodies of the instant invention were selected using a panning procedure that utilized a soluble form of the HCV E2 glycoprotein to select for Fab molecules specific for the HCV E2 antigen.

Methods for producing an intact immunoglobulin from isolated Fab fragments by combining Fab fragments with an Fc domain are known to those skilled in the art. The term "antibody" is used herein to refer to intact immunoglobulin molecules and immunologically active portions of immunoglobulin molecules. Exemplary antibody molecules are intact immunoglobulin molecules, substantially intact immunoglobulin molecules, and portions of an immunoglobulin molecule, including antigen binding fragments i.e. Fab, Fab', F(ab')$_2$, Fd, F(v), and sFv, as well as chimeric antibody molecules thereof, which exhibit immunological binding properties of the parent antibody molecule.

The terms "immunological binding affinity" and "immunoreactive" as used interchangeably herein, refer to the non-covalent interactions of the type which occur between an immunoglobulin molecule and an antigen for which the immunoglobulin is specific. The affinity of immunological binding interactions may be expressed in terms of the dissociation constant ($K_d$) of the interaction, wherein a smaller $K_d$ represents a greater affinity. Table 2 shows that of the five monoclonal antibodies directed against HCV-E2, two have particularly high affinity (HCV#4 and HCV#7). Immunological binding properties of selected antibodies may be quantified using methods well known in the art. One such method entails measuring the rates of antigen-binding site/antigen complex association and dissociation, wherein those rates depend on the concentrations of the complex partners, the affinity of the interaction, and geometric parameters that equally influence the rate in both directions. (See, Davies et al. (1990) *Ann. Rev. Biochem.*, 59:439–73).

The amino acid sequences of the variable regions of the γ1 chain of the five clones of the present invention (HCV#1, HCV#4, HCV#7, HCV#12, and HCV#13) are shown in FIG. 1 as SEQ ID NO:1, SEQ ID NO:2, SEQ ID NO:3, SEQ ID NO:4, and SEQ ID NO:5. Each of SEQ ID NOs:1–5 consists of a continuous amino acid sequence comprising three consecutive CDRs flanked by four FRs, wherein the amino acid sequence begins at the N-terminal with FR1 and continues through CDR1, FR2, CDR2, FR3, CDR3, ending at the C-terminal with FR4.

The term "FR" refers to "framework regions," which are conserved sequences flanking the three highly divergent stretches within the V regions of the heavy and light chains, referred to as "hypervariable regions". In an antibody molecule, the N-terminal antigen-binding surface is complementary to the three-dimensional surface of a bound antigen and comprises the three hypervariable regions of the heavy chain; the three hypervariable regions of the light chain form relative to each other in three-dimensional space. The three hypervariable regions of each of the heavy and light chains are referred to as "complementarity-determining regions," or "CDRs".

As used herein, the term "FR set" refers to the four flanking amino acid sequences which frame the CDRs of a CDR set of a heavy or light chain V region. Some FR (framework region) residues may contact bound antigen; however, FRs are primarily responsible for folding the V region into the antigen-binding site, particularly the FR residues directly adjacent to the CDRs.

The term "CDR set" refers to the three hypervariable regions of a heavy or light chain V region. Proceeding from the N-terminus of a heavy or light chain, these complementarity-determining regions are denoted as "CDR1", "CDR2," and "CDR3," respectively. CDRs are involved in antigen-antibody binding, and the CDR3 comprises a particularly unique region specific for antigen-antibody binding. An antigen-binding site, therefore, may include six CDRs, comprising the CDR set from each of a heavy and a light chain V region.

Currently, there are six known distinct genotypes of HCV with multiple distinct subtypes which have been identified based on phylogenetic analyses (Houghton, M. (1996) *Fields Virology*, 3$^{rd}$ Edition, Fields et al., eds., Lippencott-Raven Publishers, Philadelphia, Pa.; Simmonds et al., *J. Gen. Virol.*, (1993) 74:2391–99). Of the five antibody molecules where γ1 chain amino acid sequences are shown in FIG. 1, four novel human monoclonal antibody molecules specific to the HCV E2 envelope glycoprotein, are "cross-genotype reactive", i.e. the antibody molecule which specifically binds to an E2 antigenic determinant of HCV isolates from at least two genotypes.

The instant invention therefore also relates to nucleic acid molecules encoding the CDR and FR sets of the γ1-chain amino acid sequences shown in SEQ ID NO:1 through SED ID NO:5. The DNA constructs encoding five monoclonal antibodies, wherein each plasmid contains the γ1 heavy chain (Fd portion) and κ light chain genes in pComb3H vector, have been deposited with the American Type Culture Collection (ATCC) on Nov. 30, 2000 and have ATCC Patent Deposit Designation numbers: PTA-2747; PTA-2748; PTA-2749; PTA-2745; PTA-2746.

The following biological material has been deposited in accordance with the terms of the Budapest Treaty with the American Type Culture Collection (ATCC), 10801 University Blvd., Manassas, Va. 20110-2209, USA, on the date indicated:

| Biological material | Designation No. | Date |
|---|---|---|
| Plasmid: HCV # 12 | PTA-2745 | Nov. 30, 2002 |
| Plasmid: HCV # 13 | PTA-2746 | Nov. 30, 2002 |
| Plasmid: HCV # 1 | PTA-2747 | Nov. 30, 2002 |
| Plasmid: HCV # 4 | PTA-2748 | Nov. 30, 2002 |
| Plasmid: HCV # 7 | PTA-2749 | Nov. 30, 2002 |

The present invention also relates to variations of these nucleic acid sequences due to degeneracy of the genetic code. The coding sequences for the heavy and light chain portions of the Fab molecules may be isolated or synthesized and may be cloned into any suitable vector or replicon for expression. Examples of suitable vectors include bacterial, mammalian, yeast, and viral expression systems.

The Fab molecules of the present invention may also be produced using conventional methods of protein synthesis, based on the ascertained amino acid sequences.

The invention further relates to the phage display library described herein from which these human monoclonal antibodies are obtained. This library has been deposited with the American Type Culture Collection (ATCC) on Nov. 30, 2000 and has ATCC Patent Deposit Designation number: PTA-2750. The invention further relates to methods of making human monoclonal antibodies from the deposited phage display library. One skilled in the art has knowledge of the method for isolating a monoclonal antibody from the phage display library. In a preferred embodiment, the method involves (1) using immunoaffinity techniques such as panning to select phage particles that immunoreact with a pre-selected antigen; (2) infecting bacteria with the selected phage particles; (3) preparing and analyzing the phagemid DNA from the colonies recovered; and (4) expressing and purifying soluble Fab fragments from clones of interest for further analysis. Of course, the skilled artisan would readily understand that the pre-selected antigen used in screening could be an HCV E2 protein or peptide fragment, or any other protein of HCV (or peptide fragment thereof) other than E2 such as the E1 and core structural proteins or the non-structural proteins. By using the method disclosed above, additional human monoclonal antibodies to HCV, or to any other pathogens that may exist in the individual from whose RNA the library was prepared, may be isolated from the library of the instant invention.

The invention also relates to the use of the five monoclonal antibodies, whose γ1 chain sequences are shown in SEQ ID NOs:1–5, or those antibodies directed against HCV obtained from the deposited phage display library, as diagnostic agents. The antibodies may be used as an in vitro diagnostic agent to test for the presence of HCV in biological samples. In particular, the novel specific binding molecules of the present invention may be used in highly sensitive methods for screening and identifying individuals carrying and/or infected with HCV, as well as for screening for HCV-contaminated blood or blood products. The present binding molecules may also be used in assays for monitoring the progress of anti-HCV therapies in treated individuals, and for monitoring the growth rate of HCV cultures used in research and investigation of the HCV agent.

In one embodiment, a sample such as biological fluid or tissue obtained from an individual is contacted with a diagnostically effective amount of one or more of the human monoclonal antibodies of this invention under conditions which will allow the formation of an immunological complex between the antibody and the HCV antigen that may be present in the sample. The formation of an immunological complex, which indicates the presence of HCV in the sample, is then detected by immunoassays. Such assays include, but are not limited to, radioimmunoassays, Western blot assays, immunofluorescence assays, enzyme immunoassays, chemiluminescence assays, immunohistochemical assays, and the like, wherein a "label", as used herein referring to a detectable compound or composition which is conjugated directly or indirectly to the antibody, may be used for diagnostic purposes. The label may itself be detectable (e.g., radioisotope labels or fluorescent labels) or, in the case of an enzymatic label, may catalyze chemical alteration of a substrate compound or composition which is detectable.

As immunotherapies and immunoprophylactics are based on virus-neutralizing antibodies, the antibodies of the instant invention are preferably neutralizing antibodies and more preferably, neutralizing antibodies which are immunoreactive with E2 antigens from HCV isolates belonging to different genotypes. There are several in vitro assays known in the art which may be used to assess the capacity of a given antibody to have neutralizing activity. For example, the inhibition of binding of E2 to CD81 by the monoclonal antibodies of the present invention (See Table 3), is an indicator of potential neutralizing activity in vitro. In addition, a neutralization of binding (NOB) assay such as that described in Example 6 may be used to estimate HCV neutralizing antibodies, and to evaluate inhibition of the binding of HCV to human cells. FIG. 2 shows the results of a NOB assay in which the HCV#4 monoclonal antibody and experimental NOB positive controls all inhibit binding of HCV to cells.

The invention therefore also relates to the use of the antibodies of the present invention as pharmaceutical compositions for either prophylactic or therapeutic purposes. Such compositions are thus used as immunoprophylactic or immunotherapeutic agents.

When supplied prophylactically, a pharmaceutical composition(s) of the invention is provided in advance of any exposure to any one or more of the HCV strains or in advance of any symptoms due to infection of the viruses. The prophylactic administration of a pharmaceutical composition(s) of the invention serves to prevent or attenuate any subsequent infection of these viruses in a mammal. For therapeutic use, a pharmaceutical composition(s) of the invention is provided at (or shortly after) the onset of infection or at the onset of any symptom of infection or any disease or deleterious effects caused by these viruses. The therapeutic administration of the pharmaceutical composition(s) serves to attenuate the infection or disease. The pharmaceutical composition(s) of the present invention may, thus, be provided either prior to the anticipated exposure to the hepatitis C virus or after the initiation of infection.

Alternatively, genes encoding the recombinant antibodies may be introduced into a suitable mammalian host cell for expression or co-expression using a number of virus-based systems which have been developed for gene transfer into mammalian cells. For example, retroviruses provide a convenient means for gene delivery systems. A selected nucleotide sequence encoding a single chain $V_H$ or $V_L$ domain polypeptide may be inserted into a vector and packaged in retroviral particles using techniques known in the art (Marasco et al. (1999) *J. Immunol. Meth.* 231:223–238). The recombinant virus may then be isolated and delivered to a subject. A number of suitable retroviral systems have been described (U.S. Pat. No. 5,219,740; Miller (1990) *Hum. Gene Therapy*, 1:5–14; Scarpa et al (1991) *Virology*. 180:849–52; Burns et al. (1993) *Proc. Natl. Acad. Sci. USA*, 90:8033–7; and Boris-Lawrie and Temin (1993) *Curr. Opin. Genet. Develop.*, 3:102–9. Additionally, expression vectors derived from adenovirus, herpes or vaccinia viruses, or from various bacterial plasmids can be used for the delivery of nucleotide sequences to a target organ, tissue, or cell population. Methods, which are well known to those skilled in the art, may be used to construct expression vectors containing sequences encoding one or more recombinant antibodies along with appropriate transcriptional and translational control elements. These methods include in vitro recombinant DNA techniques, synthetic techniques, and in vivo genetic recombination. Such techniques are described in J. Sambrook et al., 1989, *Molecular Cloning: A Laboratory Manual*, Cold Spring Harbor Press, Plainview, N.Y. and in F. M. Ausubel et al., 1989, *Current Protocols in Molecular Biology*, John Wiley & Sons, New York, N.Y.

The preparation of pharmaceutical compositions containing one or more antibodies, antibody fragments, sFv molecules, or combinations thereof, as the active ingredient is generally known to one skilled in the art. Typically, such compositions are prepared as injectables (e.g. either as liquid solutions or suspensions, or as solid forms, suitable for solution or suspension in liquids prior to injection). The compositions will also generally include one or more "pharmaceutically acceptable excipients or vehicles" such as water, saline, dextrose, glycerol, ethanol, or the like and combinations thereof. In addition, minor amounts of auxiliary substances, such as wetting or emulsifying agents, pH buffering substances, and the like, may be present in such vehicles.

A therapeutically effective amount of a monoclonal antibody for individual patients may be determined by titrating the amount of antibody given to the individual to arrive at the therapeutic or prophylactic effect while minimizing side effects. The amount of composition to be delivered depends on the subject being treated, the capacity of the subject's immune system to mount its own immune responses, and the degree of protection desired. The exact amount necessary will vary depending on the age and general condition of the individual to be treated, the severity of the condition being treated and the particular anti-HCV agent selected and its mode of administration, among other factors. One skilled in the art may readily determine an appropriate effective amount. Therefore, a "therapeutically effective amount" of the composition will be sufficient to bring about treatment or prevention of HCV disease symptoms. The effective amount may be determined by measuring the amount of HCV following administration of the composition. Levels of HCV may be measured by in vitro assays known in the art such as RT-PCR. The plasma concentration of antibodies for individuals receiving the treatment is typically between 0.1 $\mu$g/ml to 100 $\mu$g/ml. In general, it is desirable to provide the recipient with a dosage of antibodies which is in the range of from about 5 mg/kg to about 20 mg/kg body weight of the mammal, although a lower or higher dose may be administered. Additionally, inocula typically contain peptide concentrations of about 1 microgram to about 50 milligrams per inoculation (dose), preferably about 10 micrograms to about 10 milligrams per dose, most preferably about 100 micrograms to about 5 milligrams per dose.

The monoclonal antibodies of this invention may be administered via one of several routes including, but not limited to, intravenous, intraperitoneal, intramuscular, subcutaneous, transdermal, and the like. In addition, the pharmaceutical compositions may be administered as an immunoprophylactic in a single or multiple dose schedule or as an immunotherapy in a multiple dose or continuous dose schedule. A multiple dose schedule is one in which a primary course of treatment may be with more than one separate dose, preferably 1–10 doses, followed by other doses given at subsequent time intervals as needed to maintain or reinforce the action of the compositions. Thus, the dosage regime will also, at least in part, be determined based on the particular needs of the subject to be treated and will be dependent upon the judgement of the administering practitioner.

The invention therefore also relates to the use of neutralizing monoclonal antibodies of the invention in passive immunotherapy of HCV infection. In addition to antibodies comprising intact immunoglobulin molecules, substantially intact immunoglobulin molecules and portions of immunoglobulin molecules, and chimeric antibody molecules thereof, there are several therapeutically useful molecules known in the art which comprise antigen-binding sites that are capable of exhibiting immunological binding properties of an antibody molecule. One such molecule is a Fab molecule which comprises a heterodimer that includes an intact antigen-binding site. The enzyme pepsin may cleave IgG into several fragments including, a "F(ab')$_2$" fragment which comprises two antigen-binding sites. An "Fv" fragment may be produced by preferential proteolytic cleavage of an IgM immunoglobulin molecule, and sometimes of IgG or IgA immunoglobulin molecules. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. (See Inbar et al. (1972) *Proc. Natl. Acad. Sci. USA*, 69:2659–62; Hochman et al. (1976) *Biochem.*, 15:2706–10; and Ehrlich et al. (1980) *Biochem.*, 19:4091–6). When used in passive immunotherapy, the patient is administered a therapeutically effective amount of one or more neutralizing human monoclonal antibodies. The passive immunotherapy of this invention may be practiced on individuals infected with HCV, or individuals at risk of HCV infection.

The present invention therefore relates to pharmaceutical compositions comprising at least one antibody of the group comprising the antibodies of the invention and additional antibodies derived from the phage display library, and a pharmaceutically acceptable carrier where such carriers may include physiologically acceptable buffers, for example, saline or phosphate buffered saline.

The present invention further relates to anti-idiotypic antibodies to the monoclonal antibodies of this invention. In one embodiment, an anti-idiotypic antibody may be prepared by immunizing a host animal with a monoclonal antibody of this invention by methods known to those of skill in the art. To eliminate an immunogenic response to the Fc region, antibodies produced by the same species as the host animal may be used or the Fc region of the administered antibodies may be removed. The anti-idiotypic antibodies produced may be used to prepare pharmaceutical compositions rather than using the monoclonal antibodies of this invention.

The antibodies of the invention and/or those obtained from the phage display library may be supplied in the form of a kit, alone, or in the form of a pharmaceutical composition.

The practice of the present invention employs, unless otherwise indicated, conventional methods of virology, microbiology, molecular biology and recombinant DNA techniques within the skill of the art. Such techniques are explained fully in the literature. See, e.g., Sambrook et al. *Molecular Cloning: A Laboratory Manual*, (2$^{nd}$ Edition, 1989); *DNA Cloning: A Practical Approach*, vol. I & II (D. Glover, ed.); *Oligonucleotide Synthesis*, (N. Gait, ed., 1984); *Nucleic Acid Hybridization*, (B. Hames & S. Higgins, eds., 1985); *Transcription and Translation*, (B. Hames & S. Higgins, eds., 1984); *Animal Cell Culture*, (R. Freshney, ed. 1986); Perbal, *A Practical Guide to Molecular Cloning*, (1984); *Fundamental Virology*, 2$^{nd}$ Edition, vol. I & II (B. N. Fields and D. M. Knipe, eds.).

The present invention will now be described by way of examples, which are meant to illustrate, but not limit, the scope of the invention.

EXAMPLES

The Examples herein are meant to exemplify the various aspects of carrying out the invention and are not intended to limit the scope of the invention in any way. The Examples do not include detailed descriptions for conventional methods employed, such as in the construction of vectors, the insertion of cDNA into such vectors, or the introduction of the resulting vectors into the appropriate host. Such methods are well known to those skilled in the art and are described in numerous publications, for example, Sambrook, Fritsch, and Maniatis, *Molecular Cloning: a Laboratory Manual*, 2$^{nd}$ Edition, Cold Spring Harbor Laboratory Press, USA, (1989).

Example 1

Donor

Bone marrow was aspirated from the patient H, an asymptomatic patient who is chronically infected with HCV. The bone marrow lymphocytes and plasma cells were separated on a Ficoll gradient and stored as a viable single cell suspension in 10% dimethyl sulfoxide, 10% fetal calf serum, and RPMI 1640 medium (BioWhittaker; Walkersville, Md.) in liquid nitrogen.

Example 2

Construction of γ1/κ Antibody Phage Library

Total RNA was extracted from ~10$^8$ bone marrow lymphocytes and plasma cells (RNA Isolation Kit; Stratagene) and mRNA was reverse transcribed into cDNA using an oligo (dT) primer (Gibco/BRL; Rockville, Md.). The cDNAs were amplified by PCR using rTth DNA polymerase (Perkin Elmer; Gaithersburg, Md.). Thirty cycles of 94° C. for 15 s, 52° C. for 50 s, and 68° C. for 90 s were performed. Patient κ-chain genes were amplified using primers specific for the human κ-chain genes. Fd segments (variable and first constant domains) of the human γ1-chain genes were amplified with nine family-specific human V$_H$ primers recognizing the 5' end of the genes (Barbas et al., *Proc. Natl. Acad. Sci. USA*, 88:7978–82, 1991; Persson et al., *Proc. Natl. Acad. Sci. USA* 88:2432–6, 1991).

The amplified κ-chains were cloned into the pComb3H phage display vector as described by Williamson et al. (*Proc. Natl. Acad. Sci. USA*, 90:4141–5, 1993; erratum *Proc. Natl. Acad. Sci. USA*, 91:1193, 1993). The amplified γ1-chains were cloned into pGEM-T cloning vector (Promega; Madison, Wis.) via the additional adenosine nucleotide added by the rTth DNA polymerase at the 3' ends of the PCR product. The γ1-pGEM-T clones were transformed into *Escherichia coli* XL-1 Blue (Stratagene; La Jolla, Calif.) and expanded into a volume of 2 liters by solid phase amplification as described in Glamann et al. (*J. Virol.*, 72:585–92, 1998). The γ1-pGEM-T library was digested with Xho I and Spe I (Boehringer Mannheim; Nutley, N.J.), and ligated into the κ-chain pComb3H library, also digested with Xho I and Spe I. The ligated products were transformed into *E. coli* XL-1 Blue. Transformants were expanded into a volume of 2 liters by solid phase amplification. The final library of 1.9×10$^7$ clones was stored in 12.5% glycerol-LB broth at −80° C. until use.

In all panning experiments and enzyme-linked immunosorbant assays (ELISA), recombinant soluble, truncated E2 protein expressed in CHO cells (Lesniewski et al., *J. Med. Virol.*, 45:415–22, 1995) was diluted to 1μg/ml in 50 mM sodium carbonate buffer (pH 9.6), and adsorbed to EIA/RIA A/2 plates (Corning Costar; Acton, Mass.) overnight at 4° C. Fabs were detected with goat anti-human IgG (H+L)-specific antibody (Pierce; Rockford, Ill.). This was coated to microtiter wells at a dilution of 1:1000, in 50 mM sodium carbonate buffer (pH 9.6), as above.

The combinatorial library screening was performed as described previously by Barbas et al. (*Proc. Natl. Acad. Sci. USA*, 88:7978–82, 1991) and Williamson et al. (*Proc. Natl. Acad. Sci. USA*, 90:4141–5, 1993; erratum *Proc. Natl. Acad. Sci. USA*, 91:1193, 1993). Approximately 10$^9$ bacteria from the library stock were inoculated into Luria-Bertani (LB) broth (Gibco/BRL; Rockville, Md.) supplemented with 100 μg/ml ampicillin and 1% (v/v) glucose (Sigma; St. Louis, Mo.), amplified and then infected with helper phage, VCS M13 (Stratagene; La Jolla, Calif.), at a multiplicity of infection of 50, to produce the library displayed on the surface of phage particles. Phage were panned on HCV E2-coated ELISA wells; in all, three rounds of panning were performed. After amplification of the selected library, the phagemid DNA was extracted and the vector modified by restriction enzyme digestion to remove the bacteriophage coat protein III-encoding region of the phage (Bender et al. *Hum. Antibodies Hybridomas*, 4:74–9, 1993). The phagemid DNAs were religated and transformed into *E. coli* XL-1 Blue (Stratagene) to produce soluble Fabs. Colonies were inoculated into LB broth in individual wells of a microtiter plate and incubated at 30° C. overnight. Fab production was induced according to Glamann et al. (*J. Virol.*, 72:585–92, 1998), and the bacterial supernatants were tested by ELISA for reactivity with E2 and for the presence of Fab.

Example 3

FAB Production and Analysis of FAB Specificity

Bacterial culture and Fab fragment purification were carried out as described by Glamann et al. (*J. Virol.*, 72:585–92, 1998). Protein concentrations were determined by both dye binding assay (BioRad; Hercules, Calif.) and $A_{280\,nm}$ (using the extinction co-efficient of 1.4 optical density units equivalent to 1.0 mg/ml). The Fab purity was determined by polyacrylamide gel electrophoresis with colloidal Coomassie blue staining (Sigma). The purified Fabs were diluted in sodium bicarbonate buffer (pH 9.0), and biotinylated at 4° C. as per the manufacturer's protocol (Pierce). After biotinylation, the Fabs were dialyzed against phosphate buffered saline (PBS) overnight at 4° C., and concentrated in Centricon-30 concentrators (Amicon/Millipore; Bedford, Mass.) as required.

ELISA analysis was performed by coating ELISA microtiter plates with protein antigens. Specifically, 1 μg/ml of the protein antigen HCV E2 and 10 μg/ml of non-specific proteins [e.g. thyroglobulin, lysozyme, glyceraldehyde-3-phoshate, chicken albumin, and cytochrome C (Sigma)] were used to coat the microtiter plates. Antigen-coated wells were blocked for 1 hr at room temperature with 3% bovine serum albumin (BSA)-PBS, washed twice with PBS-Tween 20 (0.05% (v/v)), and 50 μl of crude Fab was added to the wells. After 1 hr incubation at 37° C., the plates were washed four times with PBS-Tween 20. Bound Fab was detected with 1:5000 dilution of a goat anti-human IgG (Fab-specific) alkaline phosphatase-labeled secondary antibody (Sigma). The assay color was developed with 1 mg/ml p-nitrophenyl phosphate (Sigma) in diethanolamine buffer (Pierce). Optical density was determined at 405 nm with a reference wavelength of 650 nm.

Example 4

Nucleic Acid Sequencing, Analysis, and BST N1 Fingerprinting of HCV-Specific Fab Clones Nucleic acid sequencing was performed with the ABI PRISM Dye Terminator Cycle Sequencing Ready Reaction kit by using Ampli-Taq DNA Polymerase (Perkin-Elmer; Gaithersburg, Md.) with the following sequencing primers: heavy chain, 5'-ATTGCCTACGGCAGCCGCTGG-3' (HC1; SEQ ID NO:6) and 5'-GGAAGTAGTCCTTGACCAGGC-3' (HC4; SEQ ID NO:7); κ chain, 5'-ACAGCTATCGCGATTGCAGTG-3' (LC1; SEQ ID NO:8) and 5'-CACCTGATCCTCAGATGGCGG-3' (LC4; SEQ ID NO:9) (Glamann et al. *J. Virol.*, 72:585–92, 1998). The resulting sequences were analyzed with the Sequencher and MacVector (Oxford Molecular Group) software packages. Sequence similarity searches were performed with the V-BASE program, which is a compilation of the entire available human variable segment Ig germ line sequences (Cook et al. *Immunol. Today* 16:237:42, 1995). The results of the sequence similarity search of all known human immunoglobulin genes are summarized in Table 1. For Bst N1 (New England Biologicals; Beverly, Mass.) fingerprinting, 1 μg of plasmid DNA was digested with 1 U of enzyme overnight at 60° C. The restriction digests were analyzed on a 3% agarose gel. The restriction enzyme Bst N1, which makes frequent cuts in the human γ1-heavy chain, was used to screen for different heavy-chain sequences among the Fab clones (Marks et al., *J. Mol. Biol.*, 222:581–97, 1991). Sequence analysis confirmed the results of the Bst N1 digests, wherein only 5 unique γ1-heavy chains were identified as HCV#1, HCV#4, HCV#7, HCV#12, and HCV#13 (FIG. 1).

The specific germ-line origin of the five monoclonal antibodies was assessed by conducting a sequence similarity search of all the known human immunoglobulin genes. Two γ1-heavy chain sequences (HCV#1 and HCV#13) exhibited the most homology with the human VH4 family of germ line segments; whereas, the other three γ1-heavy chain sequences (HCV#4, HCV#7, and HCV#12) exhibited the most homology with the human VH1 family of germ line segments (Table 1). The κ-light chain sequences exhibited varied homology with the human Vκ family of germ line segments.

TABLE 1

| MAb | VH Family | D Segment | JH Segment | VK Family | JK Segment |
|---|---|---|---|---|---|
| HCV#1 | VH4 | NH* | JH6b | VKII | JK2 |
| HCV#4 | VH1 | D2-2 | JH3a | VKIV | JK2 |
| HCV#7 | VH1 | NH | JH3a | VKIII | JK5 |
| HCV#12 | VH1 | NH | JH3a | VKIII | JK2 |
| HCV#13 | VH4 | NH | JH4a | VKI | JK1 |

*NH13 No identifiable homologue

Example 5

Affinity Determination of HCV Monoclonal Antibodies

The affinities (equilibrium dissociation constant, $K_d$) of the monoclonal antibodies were determined by competition inhibition ELISA (Persson et al., *Proc. Natl. Acad. Sci. USA*, 88:2432–6, 1991; Rath et al. *J. Immunol. Meth.*, 106:245–9, 1988). Briefly, $\log_{10}$ dilutions of Fab were titrated on E2-coated wells, and the dilution at which a 10-fold decrease in Fab concentration gave a substantial reduction in the binding of the Fab was used in the competition ELISA. This concentration of Fab was then incubated for 2 hrs at 37° C. with decreasing $\log_{10}$ concentrations of E2 in solution, in E2-coated wells. The plates were washed four times with PBS/Tween-20, and bound Fab was detected using anti-human IgG (Fab-specific) alkaline phosphatase-labeled secondary antibody (Sigma) at a dilution of 1:5000. The percent reduction in $A_{405\ nm}$ value was plotted and the 50% inhibition (150) value was extrapolated. The concentration of E2 at the $I_{50}$ values represents the affinity ($K_d$) of the antibody for the antigen.

Affinities were measured for all five HCV clones, although HCV#12 was indeterminable (Table 2). The HCV E2-specific monoclonal antibodies which recognize conformational eptitopes, exhibited affinities for the soluble E2 protein, ranging from 1.6 to 40.5 nM. The $K_d$ value for four clones was determined, but the $K_d$ value of HCV#12 was most likely less than the sensitivity minimum for the assay ($<10^7$ M), and therefore indeterminable. HCV#4 and HCV#7 monoclonal antibodies had high equilibrium dissociation constants ($K_d$), 1.6 and 3.5 nM respectively.

TABLE 2

| MAb | $K_d$ (nM)* |
|---|---|
| HCV#1 | 25.5 |
| HCV#4 | 1.6 |
| HCV#7 | 3.5 |
| HCV#12 | ID |
| HCV#13 | 40.5 |

*Equilibrium dissociation constant ($K_d$)
Indeterminable (ID)

Example 6

Neutralization of Binding of a Recombinant E2 Protein to CD81 by HCV Monoclonal Antibodies The inhibition of binding between the soluble E2 protein and the putative cellular receptor, CD81 was measured. In order to analyze the blockage of CD81-E2 interactions, an assay was performed as described by Forns et al. (*Virology*, 274:75–85, 2000). The Fabs were titrated for their ability to block the CD81-E2 interaction with an irrelevant Fab, HEV#31 (Schofield et al., *J. Virol.*, 74:5548–55, 2000) used as the negative control and H79 serum (plasma from patient H, 2 years after the onset of primary HCV infection) as a positive control. The monoclonal antibodies were titered for their ability to block the binding of a recombinant CD81-thioredoxin fusion protein to recombinant soluble E2 in an ELISA format. Both monoclonal antibodies, HCV#4 and HCV#7, efficiently inhibited CD81-E2 binding (2.4 and 1.9 µg/ml, respectively). (See Table 3 for summary).

TABLE 3

| MAb | CD81-E2 Blocking titer (µg/ml) |
|---|---|
| HCV#1 | 19.5 |
| HCV#4 | 2.5 |
| HCV#7 | 1.9 |
| HCV#12 | >20.0 |
| HCV#13 | 11.0 |

Example 7

Blocking and Inhibiting HCV Monoclonal Antibody Interactions

The attachment of HCV virions to a susceptible human T-cell line, HPBMa10-2, was inhibited by two of the HCV monoclonal antibodies of the instant invention, as determined by the method of Shimizu et al. (*J. Virol.*, 68:1494–1500, 1994). Briefly, the antibody and the virus inoculum from patient H(H77 at $10^{3.5}$ 50% chimpanzee infectious doses per ml) were incubated together overnight at 4° C. This antibody-virus mixture was then added to a 1 ml suspension of $3\times10^5$ cells and incubated for 2 hrs at 37° C. After washing twice with PBS, an RNA extraction was performed prior to RT-PCR to detect cell-associated HCV genome (Shimizu et al. (1994) *J. Virol.*, 68:1494–1500).

HCV E2-specific monoclonal antibodies, anti-HVR1 (hypervariable region 1) rabbit hyperimmune (86I, 87I) or pre-immune sera (87P), and virus (H77 at $10^{3.5}$ 50% chimpanzee infectious doses per ml) were incubated together overnight at 4° C. The antibody-virus mixture was then added to a 1 ml suspension of $3\times10^5$ HPBMa10-2 cells (a susceptible human T-cell line, Shimizu et al. *J. Virol.*, 1994). The ability of the monoclonal antibodies to inhibit virus attachment to a continuous human T-cell line was determined by RT-PCR. An example of the RT-PCR data is shown in FIG. 2, a summary of the preliminary data for all five MAbs is given in the table in FIG. 2.

Example 8

Cross-Reactivity of Anti-E2 Between HCV Genotypes

To determine how broadly conserved the epitopes recognized by these monoclonal antibodies are between HCV genotypes, immunofluorescence assays were performed. Specifically, plasmids expressing the complete intracellular form of E2 from genotypes 1a, 1b, 2a, 3a, 4a, 5a, and 6a were constructed. The reactivity of the five monoclonal antibodies with the various genotypes of HCV E2 was determined by immunofluorescence staining of Huh-7 cells transfected with each of the plasmids. All of the E2 constructs comprised 20 amino acids from the C-terminus of E1 and the complete amino acid sequence of both E2 and p7. The genotype 1a construct, pE2-1a, was previously described by Forms et al. (*Vaccine,* 17:1992–2002, 1999). The genotype 1b (pE2-1b) and 2a (pE2-2a) constructs were prepared from full-length consensus infectious cDNA clones pJ4L6SF (genotype 1b; Yanagi et al. *Virology,* 244:161–72, 1998) and pJ6CF (genotype 2a; Yanagi et al. *Virology,* 262:250–63, 1999). The genotype 3a, 4a, 5a, and 6a constructs were prepared from infectious serum challenge pools (Bukh et al. *J. of Infectious Diseases,* 178:1193–1197, 1998; Bukh et al. *Intervirology,* 44:132–142, 2001).

Near confluent Huh-7 cells in 8-chambered microscope slides were transfected with 1 μg DNA per chamber according to the manufacturer's protocol using the Lipofectamine 2000 transfection reagent (Gibco/BRL). After 48 hrs incubation at 37° C., the cells were fixed and permeabilized with ice-cold acetone. The monoclonal antibodies were diluted 1:10, and H79 diluted 1:100 in 5% BSA-PBS. The slides were air-dried briefly, then the primary antibody was added and incubated in a humidified chamber for 40 minutes at room temperature. The slides were washed 3 times in PBS for 15 minutes each prior to the addition of anti-human IgG (H+L) FITC (Pierce) secondary antibody diluted 1:100. After 30 minutes incubation at room temperature in the dark, the slides were washed again prior to examination by fluorescence microscopy. Table 4 summarizes the results of the cross-genotype reactivity assays, wherein all of the monoclonal antibodies, except for HCV#12, displayed cross-reactivity with HCV E2 genotypes 1a and 1b. HCV#4 displayed cross-reactivity with E2s derived from all six of the major HCV genotypes (1a-6a). HCV#1 and HCV#13 displayed additional cross-reactivity with E2 from genotype 4a. HCV#7 also cross-reacted with E2 from genotypes 3a, 4a, and 5a. $E2_{661}$ΔHVR1 surface-expressed (genotype 1a), which lacks the hypervariable region (HVR1) of E2, was used as a positive control and was recognized by all of the monoclonal antibodies. Therefore, none of the monoclonal antibodies of the instant invention are directed to epitopes in the HVR1 of the E2 protein.

TABLE 4

| MAb | pE2 1a (H79‡)† | $pE2_{661}$ 1a ΔHVR1* | $pE2_{661}$ 1a (H00‡)* | pE2 1b† | pE2 1b (Kiso#6)* | pE2 2a† | pE2 3a† | pE2 4a† | pE2 5a† | pE2 6a† |
|---|---|---|---|---|---|---|---|---|---|---|
| HCV#1 | + | + | + | + | – | – | – | + | – | – |
| HCV#4 | + | + | + | + | + | + | + | + | + | + |
| HCV#7 | + | + | + | + | – | – | + | + | + | – |
| HCV#12 | + | + | + | – | ND | – | – | – | – | – |
| HCV#13 | + | + | + | + | ND | – | – | + | – | – |
| H79** | + | + | + | + | + | + | + | + | + | + |

'+' cells reacted with antibody, '–' cells did not react with antibody

†expressed intracellularly in Huh-7 cells

*expressed on the surface of Huh-7 cells

ND, not determined

**patient H serum sample drawn in 1979

‡H79 and H00 represent E2 clones isolated from patient H serum samples from the year 1979 and 2000 respectively (H00 was kindly supplied by Yohko Shimizu)

Kiso#6 was constructed from a Japanese isolate, and was a kind gift from Yohko Shimizu

Example 9

Epitope Mapping by Indirect Competition ELISA

Indirect competition assays are being performed to determine the relative topology of the epitopes recognized by the five MAbs on the E2 protein (FIG. 3). Competing monoclonal antibodies were titrated on E2-coated wells and an appropriate dilution was determined, giving an O.D. reading of approximately 1.0 at $A_{405\ nm}$ and at a concentration that did not saturate the antigen coated to the plate. For the competition assay, three-fold dilutions of unlabeled monoclonal antibodies were incubated in E2-coated wells for 1 hour at 37° C., then washed four times with PBS-Tween-20. A single dilution of the competing monoclonal antibodies (biotinylated chimpanzee Fab or mouse IgG) was incubated in all wells for 1 hr at 37° C. After four washes with PBS-Tween-20, the binding of the competitor monoclonal antibody was detected with either an anti-mouse IgG (H+L chain specific) alkaline phosphatase-conjugated antibody (Pierce), or by the addition of streptavidin-alkaline phosphatase (Pierce). The color was developed as described above. Based upon the competition with each other for binding to soluble E2, the MAbs were divided into two groups: (1) HCV#4 and HCV#7; and (2) HCV#1, HCV#12, and HCV#13. Therefore, the MAbs appear to be directed to at least two different epitopes on the E2 glycoprotein.

Example 10

Measurement of In Vitro Neutralization of HCV by In Vivo Monitoring in Chimpanzees Sixty-four 50% chimpanzee infectious doses ($CID_{50}$) of HCV, strain H77, will be incubated overnight at 4° C., with a mixture of human monoclonal antibodies against HCV. The next morning the mixture will be inoculated intravenously into a naive chimpanzee. The chimpanzee will be followed weekly for biochemical evidence of hepatitis (e.g. ALT, ICD, GGTP), virologic evidence of infection (e.g. RT-PCR of viremia), and serologic evidence of antibody to HCV. If the chimpanzee remains free of evidence of HCV infection for one month, the experiment will be repeated with a subset of the original pool of monoclonal antibodies.

This procedure will be repeated with different subsets of the monoclonal antibodies until the chimpanzee is infected. If necessary, additional chimpanzees will be inoculated in order to determine exactly which monoclonal antibodies are neutralizing. If all of the monoclonal antibodies prove to be neutralizing, the procedure will be repeated with monoclonal antibodies directed against other viruses as a positive control for susceptibility of the chimpanzee.

Example 11

Passive Immunoprophylaxis Against HCV in a Chimpanzee

A naive chimpanzee will be infused intravenously with one or more neutralizing HCV monoclonal antibodies. The chimpanzee will then be challenged intravenously with 64 $CID_{50}$ of HCV. The chimpanzee will be followed weekly for six months for biochemical evidence of hepatitis (e.g. ALT, ICD, GGTP), virologic evidence of infection (e.g. RT-PCR of viremia), and serologic evidence of antibody to HCV. If the chimpanzee remains free of infection, passive immunoprophylaxis will have been considered to be successful.

Example 12

Passive Immunotherapy Against Chronic HCV Infection in the Chimpanzee

A chimpanzee that is chronically infected with HCV will be infused intravenously with one or more neutralizing HCV monoclonal antibodies. The course of the HCV infection in the chimpanzee will be monitored weekly for biochemical evidence of hepatitis (e.g. ALT, ICD, GGTP), virologic evidence of infection (e.g. RT-PCR of viremia), and serologic evidence of antibody to HCV. If there is no change in the level of replication, the dose of infused antibody will be increased. If a clinical response (a decrease in the titer of viral genomes in the blood, as measured by PCR) is detected, the dose of monoclonal antibody will be adjusted to determine its minimum effective titer. The dose will be administered at intervals to the chimpanzee to determine if permanent clearing of infection may be achieved by passive immunotherapy.

---

What is claimed is:

1. A human monoclonal antibody that exhibits immunological binding affinity for a hepatitis C virus (HCV) E2 antigen, where said monoclonal antibody has a γ chain CDR3 region amino acid sequence selected from the amino acid sequences shown in SEQ ID NO:1 through SEQ ID NO:5.

2. A human monoclonal antibody that exhibits immunological binding affinity for a hepatitis C virus (HCV) E2 antigen, where said monoclonal antibody has one of the γ chain variable region amino acid sequences shown in SEQ ID NO:1 through SEQ ID NO:5.

3. A human monoclonal antibody that exhibits immunological binding affinity for a hepatitis C virus (HCV) E2 antigen, wherein a DNA construct encoding said antibody has an ATCC Accession number selected from the group consisting of ATCC Patent Deposit Designation numbers: PTA-2747; PTA-2748; PTA-2749; PTA-2745; PTA-2746.

4. The monoclonal antibody of claim 1, wherein said antibody has a γ chain CDR3 region selected from the amino acid sequence of SEQ ID NO:1 through SEQ ID NO:3 and SEQ ID NO:5, and is immunoreactive with E2 antigens from HCV genotypes 1a and 1b.

5. The monoclonal antibody of claim 1, wherein said antibody has a γ chain CDR3 region selected from the amino acid sequence of SEQ ID NO:2, and is immunoreactive to E2 antigens from HCV genotypes 1a, 1b, 2a, 3a, 4a, 5a, and 6a.

6. A nucleic acid molecule encoding heavy and light chain immunoglobulin amino acid sequences of the antibodies of claim 1, 2, or 3.

7. A DNA construct comprising the nucleic acid molecule of claim 6.

8. An antigen binding fragment of antibodies according to claim 1, 2, or 3.

9. An immunological composition comprising at least one antibody according to claim 1, 2, or 3, and a suitable excipient, diluent, or carrier.

10. An immunological composition comprising antigen binding fragments of claim 8, and a suitable excipient, diluent, or carrier.

11. A method of detecting hepatitis C virus in a biological sample, comprising:

a) contacting the sample with at least one antibody according to claim 1, 2, or 3 under conditions suitable to form an immune complex between the antibody and a hepatitis C virus antigen; and b) detecting the presence of said immune complex.

12. A method of detecting hepatitis C virus in a biological sample, comprising:

a) contacting the sample with at least one antigen binding fragment according to claim 8 under conditions suitable to form an immune complex between the antigen binding fragment and a hepatitis C virus antigen; and b) detecting the presence of said immune complex.

13. The method of claim 11, wherein the biological sample is selected from the group consisting of liver cells, bone marrow, serum, plasma, saliva, lymphocytes, or other mononuclear cells.

14. The method of claim 12, wherein the biological sample is selected from the group consisting of liver cells, bone marrow, serum, plasma, saliva, lymphocytes, or other mononuclear cells.

15. A kit for the detection of HCV, said kit comprising the monoclonal antibody according to claim 1, 2, or 3.

16. A kit for the detection of HCV, said kit comprising the antigen binding fragment according to claim 8.

* * * * *

UNITED STATES PATENT AND TRADEMARK OFFICE
CERTIFICATE OF CORRECTION

PATENT NO. : 6,924,362 B2 Page 1 of 1
APPLICATION NO. : 10/432006
DATED : August 2, 2005
INVENTOR(S) : Schofield et al.

It is certified that error appears in the above-identified patent and that said Letters Patent is hereby corrected as shown below:

Col. 21, Line 63 (approx.), Claim 6, delete "claim" and insert -- claims --, therefore.

Col. 21, Line 67 (approx.), Claim 8, delete "claim" and insert -- claims --, therefore.

Col. 22, Line 34 (approx.), Claim 9, delete "claim" and insert -- claims --, therefore.

Col. 22, Line 42 (approx.), Claim 11, delete "claim" and insert -- claims --, therefore.

Col. 22, Line 63 (approx.), Claim 15, delete "claim" and insert -- claims --, therefore.

Signed and Sealed this

Twenty-first Day of November, 2006

JON W. DUDAS
*Director of the United States Patent and Trademark Office*